(12) United States Patent
Martin et al.

(10) Patent No.: US 7,427,920 B2
(45) Date of Patent: Sep. 23, 2008

(54) POPULATION MONITORING SYSTEM

(75) Inventors: Keith Llewellyn Martin, Wiltshire (GB); Christopher S. Cox, Wiltshire (GB); Peter Douglas Biggins, Wiltshire (GB)

(73) Assignee: The Secretary of State for Defence in Her Britannic Majesty's Government of the United Kingdom of Great Britain and Northern Ireland (GB)

( * ) Notice: Subject to any disclaimer, the term of this patent is extended or adjusted under 35 U.S.C. 154(b) by 0 days.

(21) Appl. No.: 10/332,762

(22) PCT Filed: Jun. 1, 2001

(86) PCT No.: PCT/GB01/02450

§ 371 (c)(1),
(2), (4) Date: Sep. 15, 2003

(87) PCT Pub. No.: WO01/93754

PCT Pub. Date: Dec. 13, 2001

(65) Prior Publication Data

US 2004/0036599 A1    Feb. 26, 2004

(30) Foreign Application Priority Data

Jun. 6, 2000  (GB) ................................ 0013610.1

(51) Int. Cl.
*G08B 23/00* (2006.01)

(52) U.S. Cl. ............ 340/573.1; 340/539.1; 340/539.12; 340/539.26; 340/539.28; 340/601; 340/602; 340/286.07; 600/300; 600/301

(58) Field of Classification Search .............. 340/573.1, 340/407.1, 539.1, 539.19, 588, 589, 825.49, 340/825.69, 539.11, 539.12, 539.13, 539.28, 340/601, 602, 286.07, 539.26; 600/300, 600/301, 322, 587; 128/903, 920; 435/4, 435/6; 434/236, 238
See application file for complete search history.

(56) References Cited

U.S. PATENT DOCUMENTS

| | | | |
|---|---|---|---|
| 3,972,320 A | * | 8/1976 | Kalman ...................... 600/519 |
| 5,652,570 A | | 7/1997 | Lepkofker |
| 5,729,205 A | | 3/1998 | Kwon |

(Continued)

FOREIGN PATENT DOCUMENTS

DE    198 48 229 A    6/1999

(Continued)

*Primary Examiner*—Hung T. Nguyen
(74) *Attorney, Agent, or Firm*—Dean W. Russell; Kilpatrick Stockton LLP

(57) ABSTRACT

A system for monitoring a live population uses a unit as a local data collection device to derive data on the physical condition of a population member. The unit has a local processor for correlating and storing the physical condition data relative to time and a mechanism for transferring the stored data from the local processor to a remote data collection device. The remote data collection device also receives data relating to the location of the population member relative to time, and analyzes the physical condition and location data for unusual events, providing a signal on the occurrence of an unusual event. The physical condition may be derived from a sensor, which is a non-invasive sensor for measuring pulse rate, temperature and oxygen levels. The location data is provided from a locator incorporated in the unit.

28 Claims, 3 Drawing Sheets

U.S. PATENT DOCUMENTS

| | | | |
|---|---|---|---|
| 5,738,102 A * | 4/1998 | Lemelson | 600/483 |
| 5,771,001 A | 6/1998 | Cobb | |
| 5,874,897 A | 2/1999 | Klempau et al. | |
| 5,993,386 A * | 11/1999 | Ericsson | 600/300 |
| 6,057,758 A * | 5/2000 | Dempsey et al. | 340/539.12 |
| 6,102,856 A * | 8/2000 | Groff et al. | 600/301 |
| 6,113,539 A * | 9/2000 | Ridenour | 600/300 |
| 6,198,394 B1 * | 3/2001 | Jacobsen et al. | 340/573.1 |
| 6,218,122 B1 * | 4/2001 | Friend et al. | 435/6 |
| 6,287,254 B1 * | 9/2001 | Dodds | 600/300 |
| 6,402,691 B1 * | 6/2002 | Peddicord et al. | 600/300 |

FOREIGN PATENT DOCUMENTS

| | | |
|---|---|---|
| EP | 0 976 360 A | 2/2000 |
| GB | 2 205 648 | 5/1987 |
| GB | 2 285 135 | 6/1995 |
| JP | 110178800 | 7/1999 |

* cited by examiner

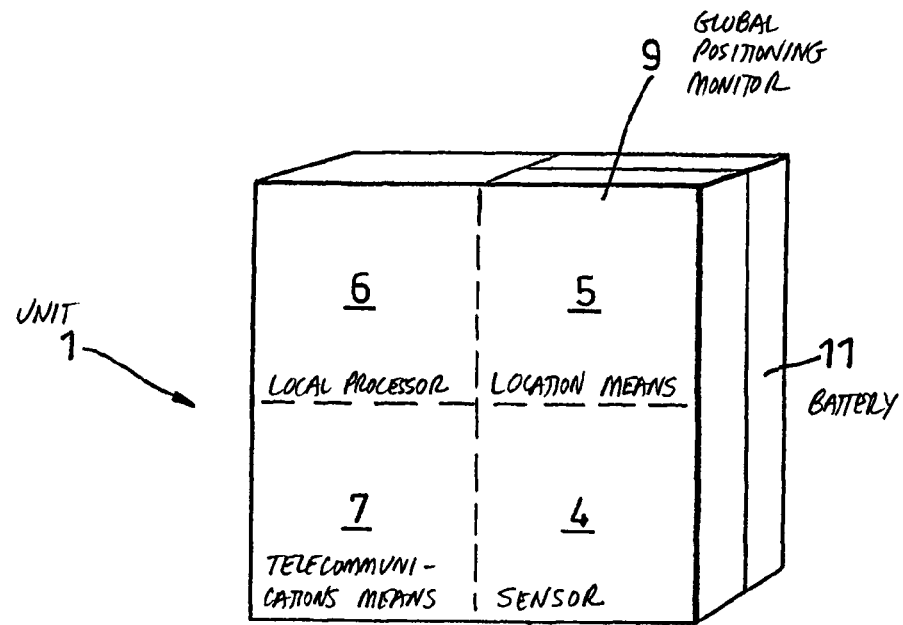
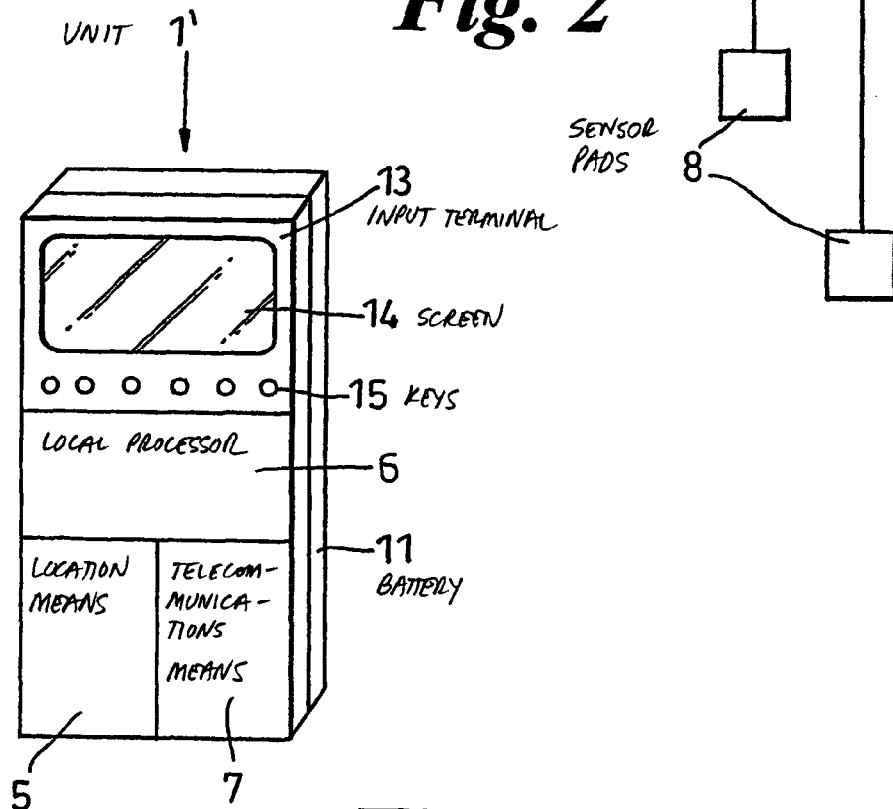
Fig. 2
Fig. 3

POPULATION MONITORING SYSTEM

This application claims priority to Great Britain Application No. 0013610.1 filed on Jun. 6, 2000 and International Application No. PCT/GB01/02450 filed on Jun. 1, 2001 and published in English as International Publication No. WO 01/93754 A1 on Dec. 13, 2001, the entire contents of which are hereby incorporated by reference.

FIELD OF THE INVENTION

This invention relates to a system for monitoring a live population, with data from the population being transferred to a remote station for analysis.

BACKGROUND OF THE INVENTION

There are various situations where there is a need for the monitoring over a period of time of the state of a live population (whether human, animal or plant) and the location of the population members. An example is where emergency service personnel are dealing with hazardous incidents. The monitoring is on the whole done by the personnel using radio or telephone communications to provide the necessary information to another human. The information provided can be analysed manually or from input to a computer, so that appropriate action can be triggered, for example in a medical emergency to provide appropriate help to the correct location. This system relies on a human initiating the communication in the first place, and may not provide accurate medical or location information. It is also difficult to correlate information from different sources to provide an overall picture of the incident, to enable hazards to be predicted.

SUMMARY OF THE INVENTION

According to the present invention, a system for monitoring a live population by monitoring at least one member of the population includes local data collection means operative to derive data relating to the physical condition of the population member, a local processor for correlating and storing the physical condition data relative to time, means for transferring the stored data from the local processor to a remote data collection means, the remote data collection means also accessing data relating to the location of the population member relative to time, and including a main processor for facilitating analysis of the physical condition and location data for identification of unusual events.

As the physical condition data and location data are correlated with time, these data can be provided accurately to the remote data collection means. The data can then be analysed for unusual events, if necessary in conjunction with data from other sources, to predict and signal the unusual events, enabling appropriate action to be taken. The monitoring system therefore performs more efficiently.

The live population may be a population of humans, animals or plants. The data relating to physical condition picks up abnormal physical symptoms, due to disease as such, injury or other factors such as environmental conditions. Analysis of this data can then be used to identify unusual events, in terms of disease, or environmental conditions.

The local data collection means and local processor are preferably incorporated in a unit. A single unit may derive data relating to physical condition from more than one population member, but it is preferred that each population member has their own unit. This enables easy monitoring of each population member separately.

The local data collection means then preferably comprises a sensor attached to the population member, and controlled by the local processor. The processor may operate the sensor continuously or intermittently. This is particularly useful where the population consists of animals or plants, but may also be useful for humans. As operation of the unit is automatic, there is no room for human error.

Alternatively, the local data collection means may comprise a manually-operable device, into which data relating to physical condition is input. Clearly, this can only be operated by humans, but is useful for deriving data from more than one population member.

Conveniently the means for transferring the stored data comprises telecommunication means, for sending radio signals or the like. A telecommunication means is preferably associated with each local data collection means. It is preferably incorporated in a unit with the local data collection means and the local processor, and is controlled by the local processor.

The operation of the local processor is preferably programmable. The telecommunication means may be operative to receive data to alter the programming of the local processor.

The unit preferably contains a power source such as batteries, operated under the control of the local processor.

Preferably the unit includes a location means operative to derive data relating to the location of the population member, and the local processor then correlates and stores the physical condition data and the location data relative to time. This provides particularly accurate physical condition and location data.

The local processor then controls operation of the location means as well, so that it is operated continuously or intermittently.

Alternatively the location means may be separate from the unit. The location means may transmit the location data to the remote data collection means. The unit may transmit the physical condition data to the remote data collection means via the location means. The location means may then correlate the physical condition and location data relative to time.

The remote data collection means may simply comprise a central computer station for receiving, storing and analysing the data. Alternatively it may comprise a central station and a number of intermediate stations which receive the data from one or more units, and relay it to the central station for storage and analysis. With this arrangement, the location means may be at the intermediate station, which correlates the location and physical condition data relative to time, and relays it to the central station. The data is preferably stored at the central station in a computer database.

The sensor for a human or animal may derive data relating to several states of the body, including pulse rate, temperature, oxyhaemoglobin, carboxyhaemoglobin and cytochrome oxidase. Monitoring is preferably by a non-invasive sensor. This may be of a near infra-red spectroscopy (NIRS) type or any other suitable type. Sensors for plants may derive data relating to temperature, water content and the like.

The location data is preferably derived from a global positioning satellite system.

BRIEF DESCRIPTION OF THE DRAWINGS

Embodiments of the invention are illustrated, by way of example only, in the accompanying drawings, in which:—

FIG. 2 is a diagrammatic illustration of a unit used in FIG. 1;

FIG. 3 is similar to FIG. 2, but shows a modified unit; and

DETAILED DESCRIPTION

Figure 1:
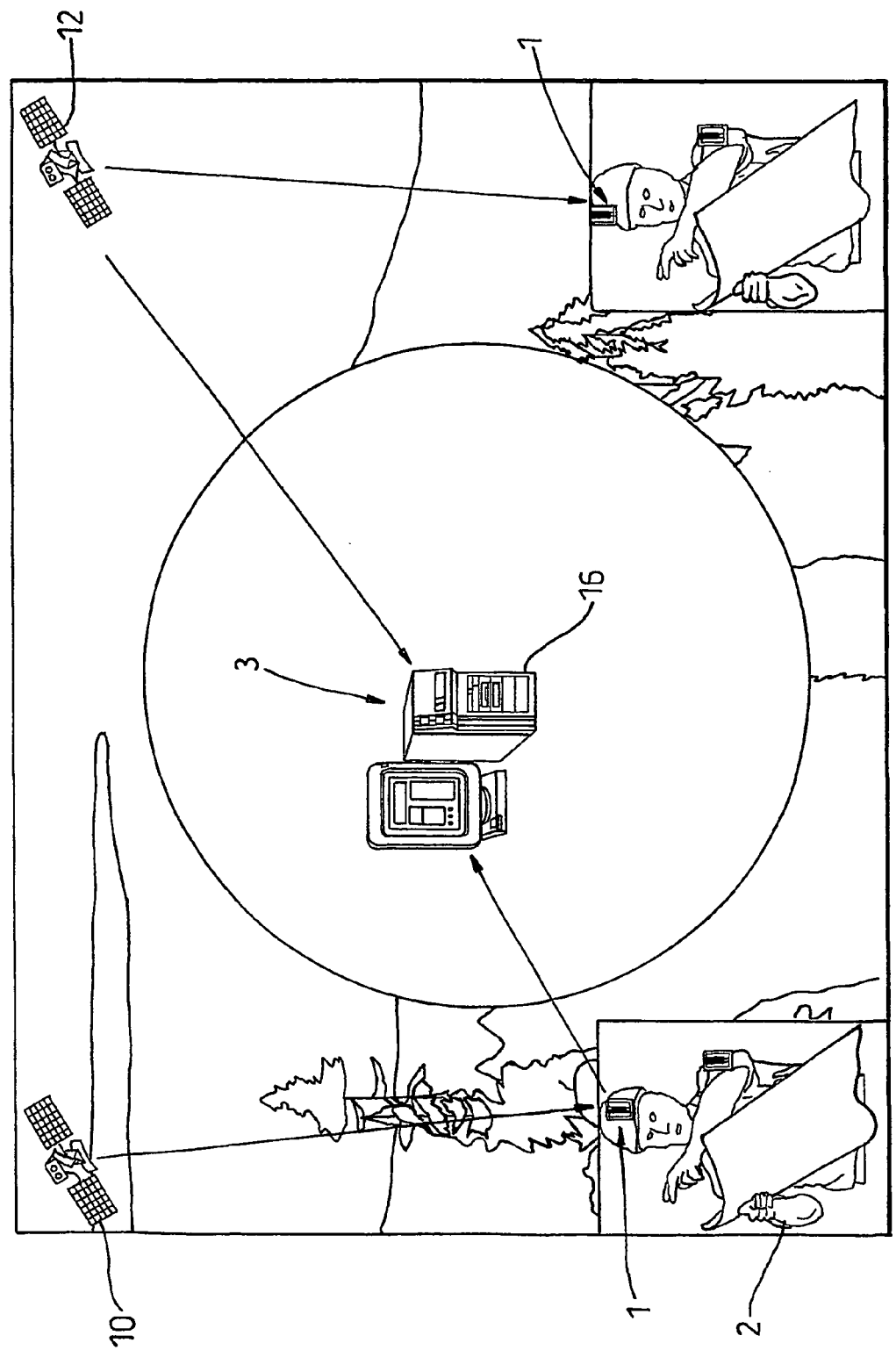
FIG. 1 is a semi-diagrammatic illustration of a population monitoring system according to the invention.

The population monitoring system of FIG. 1 has a unit 1 which derives data about the state of a population member 2 (in this case a human body), data being transferred from the unit 1 to a remote station 3 for analysis.

The unit 1 is shown in more detail in FIG. 2. It comprises a sensor 4 adapted to be attached to the body 2 to derive data relating to the physical condition of the body 2, a location means 5 which derives data relating to the location of the body 2, a local processor 6 for correlating and storing the physical data and location data relative to time, and telecommunication means 7 for transmitting the stored data to the remote station 3.

The sensor 4 is a non-invasive sensor of the near infra-red spectroscopy (NIRS) type. It has two sensor pads 8 adapted to be attached to the body 2 at spaced locations, such as the head and the arm. The sensor pads measure oxygen levels in the body 2, using near infra-red spectroscopy to monitor the levels of chromophores, whose absorbence is oxygen-dependent. Background interference from other tissues is compensated for by measuring changes in absorbence. The use of multiple wavelengths of light allows monitoring of changes in oxyhaemoglobin, carboxyhaemoglobin and cytochrome oxidase, which are all chemical states of the body relating to oxygenation levels and thus indicate the medical condition of the body 2. The sensor 4 also measures temperature and pulse data. The sensor pads 8 are non-invasively attached to the body 2 by detachable means such as tape or a band and by wires to the main part of the unit. The main part of the unit 1 is attached to the body 2 or the wearer's clothing. It can be made small and lightweight.

The main part of the unit 1 also houses the location means 5, comprising a global positioning monitor 9 which receives spatial co-ordinates from a satellite 10, as well as the time.

The data from the sensor 4 and the location means 5 is transmitted to the local processor 6, which correlates and stores it in relation to time, in a suitable electronic memory. The processor 6 is a programmable microprocessor unit adapted to operate the sensor and the location means as required. Thus, the sensor and location means may be operated continuously or intermittently. The unit 1 also includes a power source in the form of a battery 11, and the local processor 6 is also programmed to act as a power management system. Further the local processor 6 operates the telecommunication means 7 periodically to send the stored data to the remote station 3. The telecommunication means 7 sends the data by a radio signal, either directly or using a satellite 12 as a communications channel. The data could instead be transferred by telephone (terrestrial or satellite) or cable, or even manually.

FIG. 3 shows a modified unit 1' in which the sensor 4 is omitted, and the data relating to physical condition is instead derived by manual input by a human operator. Thus, the unit 1' has an input terminal 13 instead of the sensor 4 and pads 8. The terminal 13 has a screen 14 and keys 15. The processor 6 stores a number of physical conditions, one or more of which are chosen by the operator to input to the processor 6. Thus unit 1' may also be used to derive data for more than one population member. The details of the individual population members are also held by the processor 6, so that the data is related to the individuals. The construction and operation of the unit 1 is otherwise the same as that of the unit 1 of FIG. 2.

The remote station 3 comprises a data collection computer 16 including a database in which the data is stored for analysis. The computer includes a main processor for analysing the physical condition and location data for unusual events and providing a signal on the occurrence of an unusual event. The computer 16 may also have access to other, collateral, data, to assist in the identification of unusual events. The other data may be meteorological, geographic, pollution, medical or demographic databases.

The analysis of unusual events is based on the data from the units 1 or 1' and the collateral databases, chosen as required according to the expected events. The analysis uses a set of rules describing the signature of an event as a departure from a normal background level of one or more parameters. The rules assign relative significance values to the events, to enable their significance to be evaluated singly and in combination, particularly where they arise from different databases. The rules assign an overall significance value, as a probability that an unusual event has occurred. The rules may vary according to the parameters used.

An example which is useful in practice is the analysis of disease events from medical data, time, location and meteorological data. One such analysis of a particular infectious disease has been carried out retrospectively. The rules looked at the occurrence of the disease as a function of time, location (by postal area in UK) and the meteorological record.

A first rule looked at the number of cases of the disease in relation to time and meteorological conditions, to predict the number of cases which would occur in a given future time period. The rule was modified if the predicted number of cases varied significantly from the actual number.

A second rule looked at the location of the cases, that is the spatial distribution in the postal areas. An infectious disease is expected to form clusters of cases, and the degree of clustering can be used to test the randomness of the spatial distribution to determine a departure from the expected distribution.

A third rule looked for a correlation between the spatial distribution of the cases and the prevailing wind, at a given time. The rule was modified according to any correlation.

Several instances of unusual events (for example, the disease becoming epidemic) were detected by the three rules.

The monitoring system has also been used with the unit 1' of FIG. 3, to test the analysis in real time, based on manual input of physical condition, location data and meteorological data, to detect unusual events in environmental conditions, as at a hazardous incident. Here an unusual event may occur when the physical condition of several population members in a given case changes, and danger can be predicted. This enables evasive action to be taken by the individuals concerned.

Thus, the monitoring system can be used for populations, to signal unusual events. While it has been described in terms of monitoring a population of humans it would also be used to monitor populations of animals or even plants. When monitoring plants, data relating to location will be input to, or otherwise available to the central data collection computer 15, as global positioning will not be a requirement.

Figure 4:
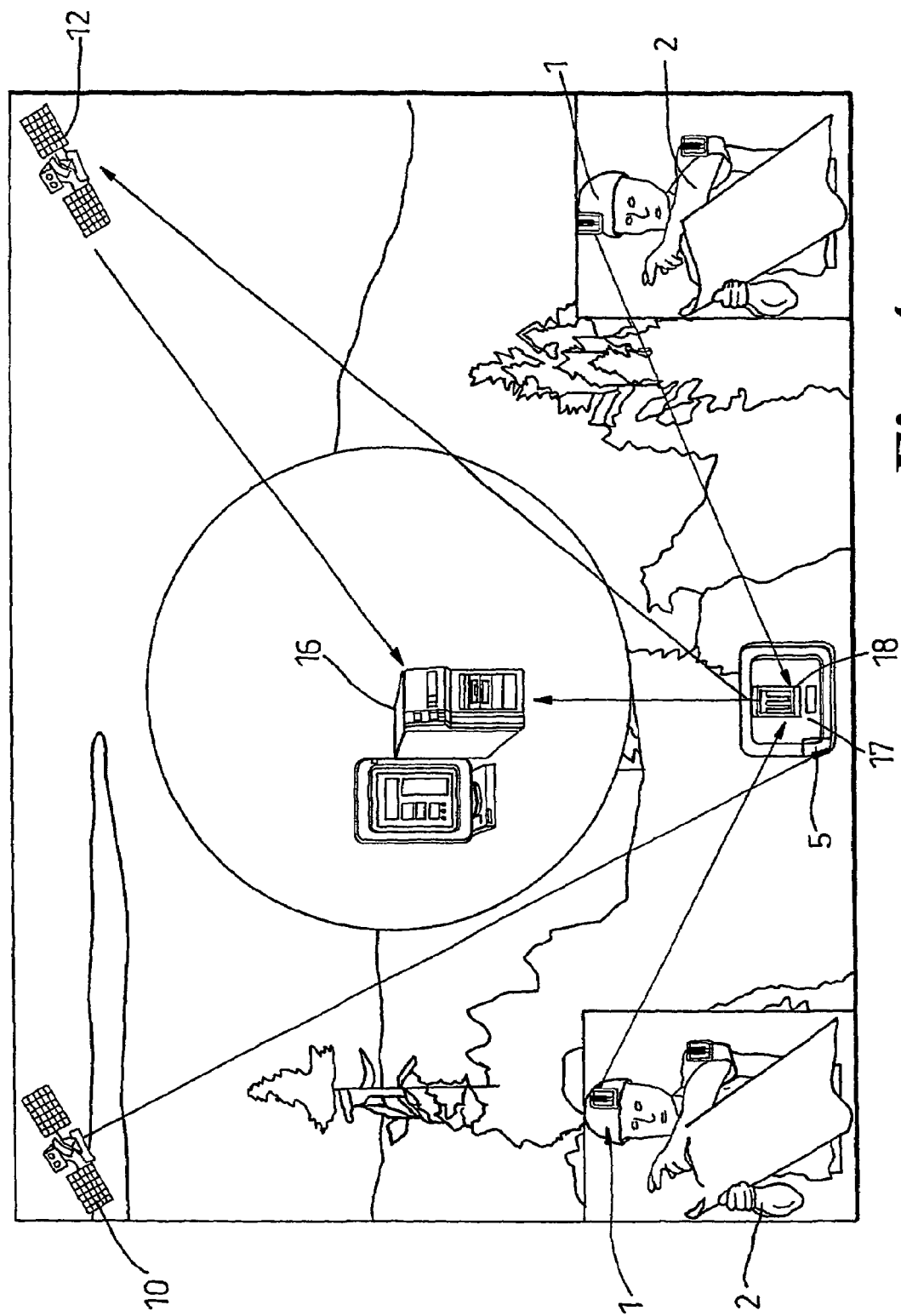
FIG. 4 is a semi-diagrammatic illustration of a modified monitoring system.

FIG. 4 shows a modified monitoring system particularly suitable for monitoring groups of population members in a given area, and corresponding reference numerals have been applied to corresponding parts. In FIG. 4, the location means 5 are provided not on the units 1, but at an intermediate or base station 17. The unit 1 therefore derives only physical conditions data, which the processor 6 correlates and stores relative to time. The processor 6 in this case provides the time information. The intermediate station serves to derive data on the location from the global positioning system. It has communication means 18 for receiving the physical condition data from the units 1, and relaying this, together with the location data, to the central data collection computer 15 for analysis. The physical condition and location data may be correlated by the intermediate station or the central computer 16. The communication means 18 preferably relays the data by a radio signal, but the data could be transferred by any suitable means.

The invention claimed is:

1. A system for predicting an epidemic disease within a live population, comprising:
    (a) local data collection means operative to derive physical condition data of a plurality of population members;
    (b) a local processor for correlating and storing the physical condition data of each of said population member relative to time; and
    (c) means for transferring the data of each of said population members stored by the local processor to a remote data collection means;
    wherein the remote data collection means is (i) operative to access information relating to the location of each of said population members relative to time and (ii) comprises a main processor programmed to analyze the physical condition data and the location information of said plurality of population members together according to a set of rules which assign a relative significance to a departure from each of a normal background level and an expected distribution of cases of the disease and an overall significance value signaling a probability of epidemic within said population.

2. A system according to claim 1, wherein the remote data collection means has access to collateral data comprising meteorological, pollution, medical, or demographic databases.

3. A system according to claim 1, wherein the remote data collection means has access to collateral data comprising a geographic database.

4. A system according to claim 1, wherein the local data collection means and the local processor are provided together in a single unit.

5. A system according to claim 4, wherein the single unit derives data relating to physical condition from more than one population member.

6. A system according to claim 5, wherein each population member is provided with a single unit.

7. A system according to claim 6, wherein the local data collection means of each single unit comprises a sensor attached to the population member and controlled by the local processor.

8. A system according to claim 7, wherein the sensor comprises a non-invasive sensor which derives data relating to oxygen levels in a human or an animal body.

9. A system according to claim 4, wherein the means for transferring the stored data comprises telecommunication means associated with the local data collection means.

10. A system according to claim 9, wherein the telecommunication means is incorporated into the single unit for control by the local processor.

11. A system according to claim 9, wherein the telecommunication means sends the stored data by radio signal.

12. A system according to claim 4, in which each single unit includes location means operative to derive information relating to the location of each population member and the local processor correlates and stores the physical condition data and the information relating to location relative to time.

13. A system according to claim 4, further comprising a location means, operative to derive data relating to the locations of the plurality of population members, which is separate from the local data collection means.

14. A system according to claim 13, wherein the location means transmits the information relating to location to the remote data collection means.

15. A system according to claim 13, wherein the means for transferring stored data transmits the stored data to the remote data collection means via the location means.

16. A system according to claim 1, wherein the local processor is programmable.

17. A system according to claim 16, wherein the local processor controls operation of the location means.

18. A system according to claim 17, wherein the remote data collection means comprises a central computer station and at least one intermediate relay station which includes a location means which transmits the information relating to location to the central station.

19. A system according to claim 1, wherein the remote data collection means comprises a central computer station.

20. A method for monitoring a live population consisting essentially of monitoring a plurality of members of said population by
    (i) collecting data relating to a physical condition of each of the plurality members by local data collection means;
    (ii) correlating and storing in a local processor each of the physical condition data of the members relative to time;
    (iii) transferring the stored physical condition of the members to a remote data collection means; and
    (iv) analyzing the transferred physical condition data of the members at the remote data collection means together with data received at the remote data collection means relating to the location of each of the members relative to time according to a set of rules which assign a relative significance to a departure from each of a normal background level and an expected distribution of one or more parameters and an overall significance value signaling a probability of epidemic disease within said population and an environmental condition hazardous to said population as a whole.

21. A method according to claim 20, in which the physical condition data of each of the members is collected by a unit including a non-invasive sensor provided to each of the members.

22. A method according to claim 21, in which the location data is derived by location means provided in said unit and both the physical condition and the location data are correlated and stored by said processor prior to transmission to said remote data collection means.

23. A method according to claim 22, in which the local processor is programmed for continuous or intermittent collection of the physical condition data and the location data.

24. A method according to claim 22, in which the transmission of the stored physical condition data and location data to the remote data collection means is periodic.

25. A method according to claim 21, in which the location data is derived by location means separate to said unit and the physical condition data is transmitted from said unit to said separate location means and both the physical condition data and location data is correlated and stored in said separate location means prior to transmission to said remote data collection means.

26. A method according to claim 21, in which the remote data collection means includes a central computer station and, optionally, a number of intermediate stations which receive and relay to the central computer station the physical condition data and the location data from one or more unit.

27. A method according to claim 21, in which the non-invasive sensor is a near infra-red spectroscopy sensor.

28. A method according to claim 20, in which the physical condition data of the members is collected by a single unit having a manually operable input device.

* * * * *